United States Patent [19]

Warren

[11] 4,223,189

[45] Sep. 16, 1980

[54] SOUND DAMPENING EARPLUG MOUNTING DEVICE

[76] Inventor: James C. Warren, 3808 S. Jasmine, Denver, Colo. 80237

[21] Appl. No.: 965,092

[22] Filed: Nov. 30, 1978

[51] Int. Cl.² ............................................. H04R 1/10
[52] U.S. Cl. ................................ 179/182 R; 181/135
[58] Field of Search ............ 179/107 E, 182 R, 182 A, 179/156 A; 181/130, 132, 133, 134, 135, 131; 128/151, 152; D2/259; D24/67

[56] References Cited

U.S. PATENT DOCUMENTS 2,904,640   9/1959   Dreher et al. ................... 179/156 A
3,431,370   3/1969   Crosby ............................. 179/182 R
3,983,336   9/1976   Malek et al. ...................... 179/107 E Primary Examiner—James W. Moffitt
Attorney, Agent, or Firm—Gary M. Polumbus

[57] ABSTRACT

An earplug mounting device individually molded to the shape of a user's ear is adapted to fit tightly therein and support a forwardly extending boom from which can be suspended audio or visual aids of various types and configurations. The earplug mounting device may be further adapted to conduct sound from audio communication devices to the inner ear while being of such construction as to dampen outside ambient noise.

5 Claims, 6 Drawing Figures

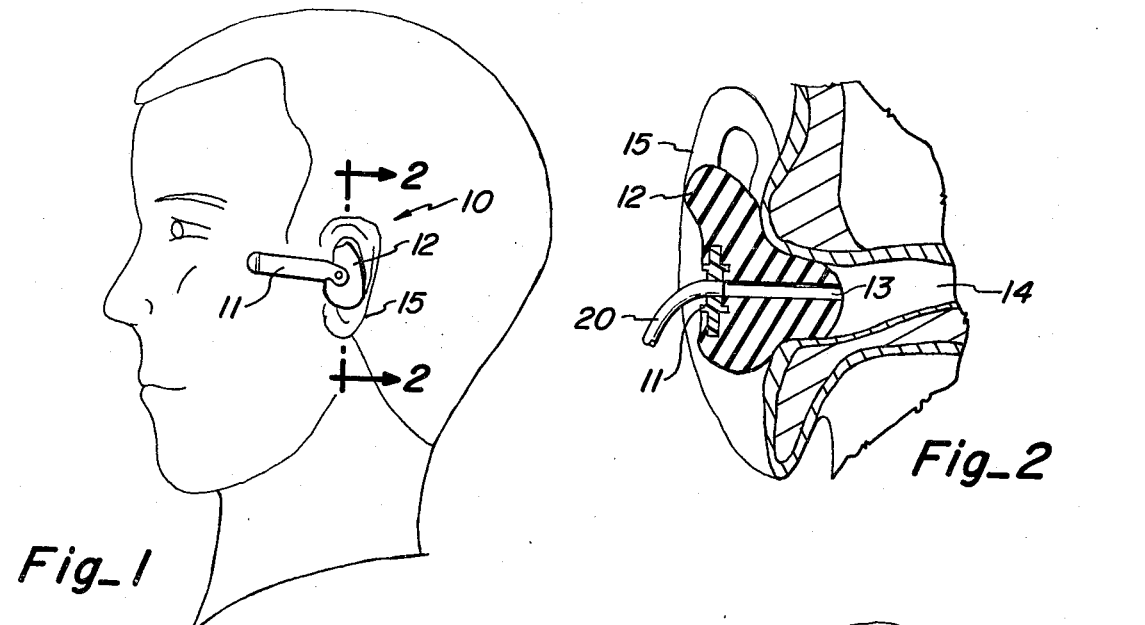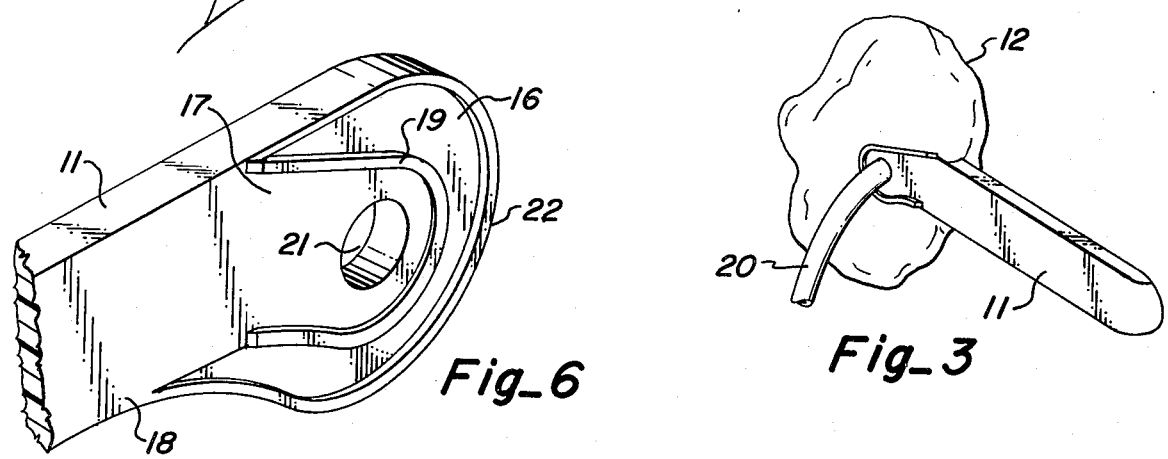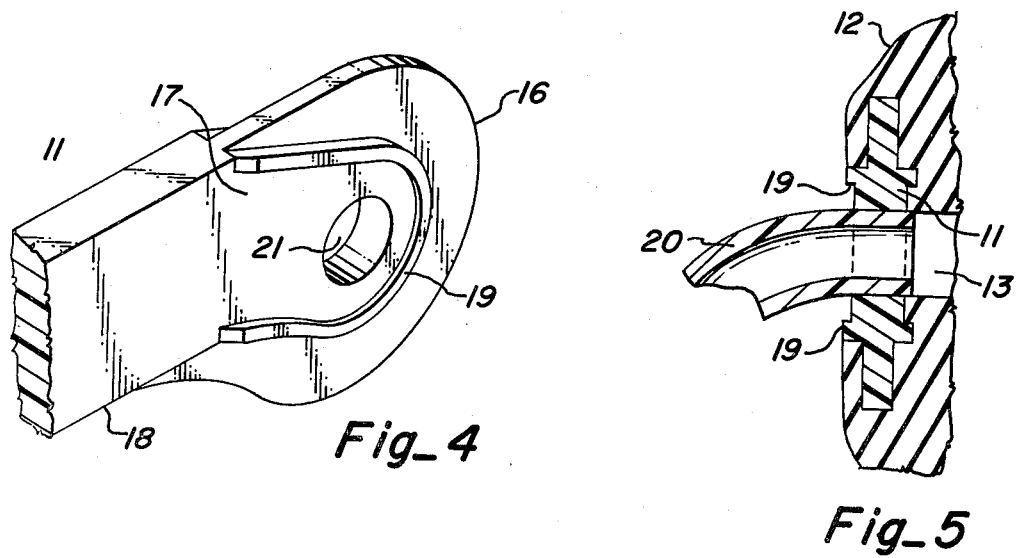

SOUND DAMPENING EARPLUG MOUNTING DEVICE

BACKGROUND OF THE INVENTION

1. Field of the Invention

The present invention relates to sound attenuating devices and particularly earplug devices which have the capability of supporting other articles such as eye glasses and various optical equipment as well as electronic communications devices and the like.

2. Description of the Prior Art

Earplugs have been used for years to attenuate sound, but only recently have such plugs gained sophistication from a comfort and/or utilitarian standpoint. Some earplugs are now being formed to contour fit a given individual's ear and some are being incorporated into other devices such as telecommunications equipment so that such equipment can be supported by the ear. Examples of such devices are found in U.S. Pat. No. 3,440,365, H. W. Bryant et al, issued Apr. 22, 1969 and U.S. Pat. No. 3,692,958, Leslie E. Basil Dymoke Bradshaw, issued Sept. 19, 1972.

A drawback to current telecommunications equipment which is supported by the ear is that the ear piece is relatively hard, to gain the support needed for whatever gear is mounted thereon, and due to the hardness, the ear piece fails to effectively dampen ambient sounds and in fact, may amplify it. This shortcoming is particularly noticeable in the aviation environment, where jet engine and aerodynamic noise levels are a constant interference with communications.

Another drawback of prior ear mounting devices for telecommunications equipment applications, which includes an ear piece that is integral with the telecommunications equipment, is that it cannot be used independently of such equipment, with other types of telecommunications equipment or for supporting other articles such as eyeglasses or other optical aids.

SUMMARY OF THE INVENTION

The earplug device of the present invention includes a main body, which may include a passageway seating a hollow tube for conducting sound, and a forwardly extending boom secured to the main body for supporting various types of articles such as eyeglasses, electronic components or the like. The main body is made from a soft pliant silicone compound that can be individually form fitted to the majority of outer ear of the user so as to conform to each variation therein. This material, which is commercially available, is such that once setting takes place, the shape of the outer ear portion of the plug and the canal portion leading to the inner ear remain throughout the life of the earplug.

The main body snugly fits into the ear of the user with the comfort that can only occur in a custom fit of a soft material that will hold a pre-set configuration. In addition the use of a silicone rubber greatly enhances sound dampening properties over hard plastic inserts.

Selected sound in the form of audio communication can be transmitted to a location very near the inner ear itself through the passageway provided through the main body. A hollow tube is inserted into the passageway and held frictionally and acoustically tight within the main body. The hollow tube is connectible to a telecommunications receiver that could be mounted on the boom or can be plugged to maintain the sound attenuation characteristics of the invention, when other applications are desired.

The forwardly extending boom is molded into the main body and cantilevered therefrom. The support boom is so constructed that various ridges extend into the main body both laterally from the boom and longitudinally along the length thereof. Once cantilevered from the main body the support boom can be adapted to receive numerous articles.

Accordingly, a general object of the present invention is to provide a comfortable, inexpensive earplug mounting device having the capability of supporting other utilitarian articles such as eyeglasses, telecommunication equipment and the like.

BRIEF DESCRIPTION OF THE DRAWINGS

FIG. 1 is a side view of the earplug device positioned in a user's ear.

FIG. 2 is an enlarged fragmentary cross-sectional view of the earplug device taken along line 2—2 of FIG. 1.

FIG. 3 is a perspective view of the earplug device.

FIG. 4 is an enlarged fragmentary perspective view of the enlarged end of the boom.

FIG. 5 is an enlarged fragmentary cross-section of the boom embedded in the main body of the earplug.

FIG. 6 is an enlarged fragmentary perspective view of an alternative embodiment of the boom.

DESCRIPTION OF THE PREFERRED EMBODIMENT

An earplug and mounting device 10 as shown in the figures, includes as elements thereof a forwardly extending boom 11, a main body 12, and an auditory passageway 13. The main body 12 is individually fitted to protrude into a particular user's auditory canal 14 and surrounds and fills the outer ear 15 in the area adjacent and surrounding the outer termination of the auditory canal. The main body 12 is light in weight and resilient for comfort, yet possesses sufficient rigidity to support the forwardly extending boom 11 and any accessory suspended therefrom. Additionally, the main body 12 should be of a material that by reason of its resiliency and pliant characteristics can act to seal off the inner ear of the user from undesirable sound, while permitting desired sound to be conducted by the passageway 13 through the auditory canal 14. The above attributes are best combined in a silicone base putty, such as the type of silicone putty manufactured by Dreve-Otoplastic, Rembrandstrabe 2, 4750 Anna Industrepart, West Germany.

The main body 12 is individually formed by initially measuring out from 2 to 5 grams of the putty. A preferable amount is approximately 2.84 grams. The putty material is flattened into a disc in the palm of the hand to a thickness approximately that of a dime. An amount of catalytic agent or activator, preferably Harterpaste which is also manufactured by Dreve-Otoplastic, within the range of 0.3 to 0.7 of grams, but preferrably 0.5 grams, is spread over the entire flat disc of putty. The putty is then rolled up into a shape simulating a jellyroll, kneaded thoroughly and quickly and rolled into a ball. It is then shaped into a cone, the apex of which is of smaller circumference than the auditory canal of the ear of the user. The cone form should have a height in the range of 25 to 40 millimeters, but preferrably 31.75 millimeters in height.

The main body 12 is then fit into the auditory canal 14 and exterior ear 15. Sufficient force is used to flatten the cone of putty into the positive mold defined by the exterior ear 15, care being taken to leave sufficient putty to receive and cover the boom 11. The boom 11 is then positioned on the main body 12 to extend generally forward toward the eyebrow and is embedded in the main body 12 in a manner which will be described in more detail later. Once the putty cures the main body and embedded boom are withdrawn from the ear.

The forwardly extending boom 11 is preferably made of plastic or other lightweight material such as Kydex plastic, manufactured by Rohm and Haas Manufacturing Company, Independence Mall West, Philadelphia, Pa. The boom is generally key-shaped having an enlarged rounded end 16 and a forwardly extending portion 18 of generally rectangular cross-section. The forwardly extending portion 18 is of greater thickness than the enlarged rounded end 16. On opposite sides of the boom 11 are half-moon curved, raised ridges 19 which separate the inner end 17 of the forward portion 18 of the boom from the rounded end 16. Each ridge 19 begins at the top of the boom, at the intersection of the forward portion 18 with the rounded end 16, and continues around a bore 21 passing through the boom at the center of the rounded end 16, and subsequently terminates at the lower edge of the forwardly extending portion 18 of the boom. The ridge 19 extends outwardly from the rounded end 16 and the forwardly extending portion 18 of the boom 11 as shown in FIG. 5, and it has been found that a satisfactory height, above the rounded end 16, for the ridge 19 is 0.060 inches. In an alternative form, (FIG. 6) a second ridge 22 is located around the peripheral edge of the enlarged rounded end 16, of the same height as the thickness of the forward extending portion 18 of the boom 11.

The preferred dimensions for the boom 11 are 2 9/16 in. in length, 7/16 in. in width and ⅛ in. in thickness. A radius of the enlarged rounded end 16 of ⅜ in. has been used, with the ridge 19 heights as previously disclosed. The ridge 19 about the inner end 17 has a radius of 3/32 in.

When the boom 11 is connected to the ear mold 12, as during the custom fitting procedure previously described, one of the continuous ridges 19 is embedded into the earplug 12. Excess putty is then smoothed over the enlarged rounded end 16 and built to a level or height equal to that of the outside facing half-moon curved ridge 19. (See FIG. 5). It will be appreciated that by use this geometry the boom 11 is cantilevered from the main body 12 in such a manner that significant lateral forces can be exerted on the end of the boom, reducing the likelihood of knocking the boom from its connection to the main body.

Once the boom 11 and the main body 12 have been mated, as previously described, the bore 21 of the boom 11 and the passageway 13 through the main body 12 are drilled or otherwise formed. The auditory passageway 13 thus created is utilized to receive a hollow tube 20 for connection to a telecommunication device. In applications other than telecommunications, the hollow tube can be plugged to maintain the sound attenuation characteristics.

The boom 11 of the earplug mounting device is adapted to receive the aforesaid visual or audio devices by any of several connection means, one of which would be a clip (not shown) over the boom 11 joining the boom to any device to which one might desire. It will be appreciated that not only does the earplug mounting form means for suspending tele-communications devices, but also in that application, prevents unwanted sound from entry into the auditory canal 14 and hence to the inner ear. This feature helps prevent hearing impairment in many of the environments where it is used. It will further be appreciated that the present mounting device is adaptable to mountings of many different types of telecommunications or visual aids.

Sound reduction characteristics of the present invention have been found by testing to be very good. The results of those findings appear in the following chart:

| | Frequency (Hz) | | | | | | | | |
| --- | --- | --- | --- | --- | --- | --- | --- | --- | --- |
| Pure-tone Frequency (Hz) | 125 | 250 | 500 | 1000 | 2000 | 3000 | 4000 | 6000 | 8000 |
| Sound Reduction (dB) | 22 | 23 | 25 | 27 | 33 | 40 | 42 | 40 | 35 |
| Standard Deviation (dB) | 4.3 | 4.4 | 3.8 | 3.6 | 4.5 | 3.9 | 4.3 | 4.6 | 4.6 |

The Sound Reduction (dB) is the difference in noise level between an unprotected ear and an ear using the present invention. The presence of an enclosed hollow tube 20, tightly held within the earplug device 10, does not diminish these results. This attenuation is comparable to head band mounted noise attenuation muffs, completely covering the outer ear.

Thus it can be readily understood that the new and improved mounting device of the present invention eliminates or avoids many of the problems inherent in prior headband devices as well as ear mounting devices. It can also be readily understood that fabrication of the present invention may be completed in a relatively short time.

While the present invention has been described with a certain degree of particularity, it is recognized that changes in the detail of the structure without departing from the spirit of the invention as becomes readily apparent by reading the attendant claims.

What I claim is:

1. An earplug mounting device for insertion into the human ear, wherein the human ear includes an outer ear and an auditory canal leading to the inner ear, comprising:
   a resilient semi-rigid main body conformably fitting within the outer ear and extending into the auditory canal; and
   a boom rigidly affixed to said main body and extending away therefrom, said boom being made of a light weight plastic material of key shaped configuration having an enlarged rounded end and a generally rectangular portion extending away from said enlarged rounded end, said enlarged rounded end having a relatively narrow thickness as compared to the generally rectangular portion of said boom, and a curved ridge on either side of said boom separating said rounded end from said generally rectangular portion, said ridge extending above said generally rectangular portion.

2. The earplug mounting device of claim 1 wherein the main body is made of a silicone putty which is formed in such a manner as to be flush with the top edge of the curved ridge of said boom, and overlie the enlarged rounded end of the boom.

3. The earplug mounting device of claim 2 wherein a second ridge, of height equal to the thickness of the forward portion of the boom, surrounds the periphery of the enlarged rounded end.

4. An earplug mounting device for insertion into the human ear, wherein the human ear includes an outer ear and an auditory canal leading to the inner ear, comprising:

a main body made of a silicone putty conformably fitting within the outer ear and extending into the auditory canal of the inner ear, said main body being formed by custom fitting said silicone putty to an individual user's ear, and a boom having an enlarged rounded end, a generally rectangular portion extending away from said rounded end, and a curved ridge on both sides of said boom, separating said rounded end and generally rectangular portion, said ridge extending above said generally rectangular portion and being flush with said main body so that said main body overlies the rounded end of the boom, said boom and main body further having a passageway therethrough and a hollow tube seated in the passageway.

5. The earplug mounting device of claim 4 wherein a second ridge, of height equal to the thickness of the forward portion of the boom, surrounds the periphery of the enlarged rounded end.

* * * * *